United States Patent
Ben-Amotz et al.

(10) Patent No.: US 8,722,057 B2
(45) Date of Patent: May 13, 2014

(54) **METHOD FOR PRODUCING β-CAROTENE RICH *DUNALIELLA* POWDER**

(75) Inventors: Ami Ben-Amotz, Gifu (JP); Nobuo Mori, Gifu (JP)

(73) Assignee: Nikken Sohonsha Corporation, Gifu (JP)

( * ) Notice: Subject to any disclaimer, the term of this patent is extended or adjusted under 35 U.S.C. 154(b) by 73 days.

(21) Appl. No.: 13/462,003

(22) Filed: May 2, 2012

(65) Prior Publication Data

US 2012/0288519 A1  Nov. 15, 2012

(30) Foreign Application Priority Data

May 10, 2011 (JP) .............................. 2011-105038
Apr. 20, 2012 (JP) .............................. 2012-096379

(51) Int. Cl.
*A61K 39/385* (2006.01)
*C12N 1/12* (2006.01)
*A61K 36/02* (2006.01)

(52) U.S. Cl.
USPC ................................. 424/195.17; 435/257.1

(58) Field of Classification Search
USPC ................... 424/195.17; 435/257.1
See application file for complete search history.

(56) References Cited

U.S. PATENT DOCUMENTS

2008/0155888 A1* 7/2008 Vick et al. ................... 44/308

FOREIGN PATENT DOCUMENTS

| JP | 60132987 | A | * | 7/1985 |
| JP | 7000147 | A | | 1/1995 |
| JP | 9000203 | A | | 1/1997 |
| JP | 2001161348 | A | | 6/2001 |
| WO | WO2005048741 | A1 | * | 6/2005 |

OTHER PUBLICATIONS

Stevens, Christian V, et al. ed. Renewable Bioresources; Scope and Modification for Non-Food Applications; John Wiley & Sons Ltd., West Sussex, England, 2004, pp. 278 and 281.*
Kanshoku, "Regarding Prevention of Hygienic Harm by Chlorella Containing Chlorophyll Degradation Products such as Pheophorbide," Notification of the Director of Environmental Health Bureau of the Ministry of Health and Welfare, May 8, 1981, No. 99 (English translation).

* cited by examiner

*Primary Examiner* — Patricia Leith
(74) *Attorney, Agent, or Firm* — Heslin Rothenberg Farley & Mesiti P.C.

(57) ABSTRACT

In a step of producing a powder product of the alga belonging to the genus *Dunaliella*, a pH adjusting step is included in which an alga belonging to the genus *Dunaliella* is allowed to be in a basic state of pH 9.5 or higher. According to the method, it is possible to provide dried *Dunaliella* powder containing β-carotene at a high content by suppressing degradation of β-carotene as an active ingredient while decreasing each of the total pheophorbide amount and the existing pheophorbide amount to a predetermined value or less, even if the total pheophorbide amount and the existing pheophorbide amount of the cultured algae belonging to the genus *Dunaliella* are higher in summer.

5 Claims, No Drawings

METHOD FOR PRODUCING β-CAROTENE RICH *DUNALIELLA* POWDER

CROSS REFERENCE TO RELATED APPLICATIONS

This application claims priority of Japanese application No. 2011-105038 filed on May 10, 2011 and Japanese application No. 2012-096379 filed on Apr. 20, 2012, the entire contents of these applications being hereby incorporated by reference herein.

BACKGROUND OF THE INVENTION

1. Field of the Invention

The present invention relates to a method for producing a powdery solid of *Dunaliella* algae containing β-carotene at a high concentration.

2. Description of the Related Art

In general, β-carotene is a representative oil-soluble organic compound of carotenoids contained in brightly colored vegetables such as a carrot, is known to be degraded into retinal by an enzyme and then oxidized into vitamin A (retinol) in a body, and is a useful compound for a human body. Furthermore, a retinoic acid obtained by further oxidization of retinol has been reported to have an anticancer activity, and therefore much more attention has been focused on β-carotene.

As a method for producing β-carotene, a production method from β-ionone by chemical synthesis and a production method by culturing algae such as *Dunaliella* algae, *Spirulina* algae, and *Chlorella* algae are known. Recently, since consumers have been becoming nature-oriented, β-carotene derived from chemical synthesis may be avoided, and therefore β-carotene derived from natural products obtained by, for example, culturing algae has been demanded.

As microalgae having a high content of β-carotene derived from natural products, *Dunaliella* is known. The algae belonging to the genus *Dunaliella* are salt-tolerant single cell green algae belonging to the phylum Chlorophyta, the class Chlorophyceae, the order Volvocales, and the genus *Dunaliella*, and are known to inhabit the Dead Sea, Israel, and Great Salt Lake, Utah, USA.

In order that a consumer can easily take or store β-carotene, a dried powder of *Dunaliella* algae, a tablet obtained by compressing and hardening the dried powder of *Dunaliella* algae, or a capsule obtained by encapsulating the dried powder of *Dunaliella* algae are known. In any states, firstly, it is necessary to dry a culture solution of *Dunaliella* algae and to form it into dried powder.

For example, Japanese Patent Laid-Open No. 1997-203 discloses that a dried powder product of the algae belonging to the genus *Dunaliella* is obtained by previously decreasing the water content of a culture solution of cultured *Dunaliella* alga body to, preferably, about 50% for easy drying, followed by being subjected to nebulization drying, vacuum drying or freeze drying.

Furthermore, Japanese Patent Laid-Open No. 2001-161348 discloses that a dried powder product of the algae belonging to the genus *Chlorella* is obtained by dehydrating a suspension of mass cultured *chlorella* by centrifugation and treating the dehydrated product in a solution of pH 5.5 containing an enzyme or polysaccharides, followed by heating and cooling and then lyophilization.

Dried powder products of the algae belonging to the genus *Dunaliella* are sold as foods. It is necessary to carry out a step of decreasing compounds that may be harmful to a human body in a step of producing a dried powder product from the harvested algae belonging to the genus *Dunaliella* in order to satisfy a predetermined safety standard.

Among others, a part of algae such as the algae belonging to the genus *Dunaliella* contains pheophorbide. Pheophorbide is hygienically harmful and causes skin disorder. Specifically, as described in the attached document to "Regarding Prevention of Hygienic Harm by *Chlorella* Containing Chlorophyll Degradation Products such as Pheophorbide" (May 8, 1981, Kanshoku No. 99, Notification of the Director of Environmental Health Bureau of the Ministry of Health and Welfare), development of photosensitive syndrome by eating of the internal organs of spring abalone and *chlorella* processed food is known. It is thought to be because pheophorbide and the like are delivered through blood to tissue cells in a living body and oxygen activated by light in the presence of this substance oxidizes a fatty acid (an arachidonic acid) and the like constituting the cell membrane so as to form lipid peroxide, and the lipid peroxide induces destruction of tissue cells of the biological membrane and other various disorders, or cause itching of the skin by increasing the permeability of the capillary vessels.

As guidelines regarding health foods in this field, the above-mentioned Notification by the Director of Environmental Health Bureau of the Ministry of Health and Welfare is known. It mentions that the existing pheophorbide amount should not exceed 100 mg %, or the total pheophorbide amount (the sum of the existing pheophorbide amount and the chlorophyllase activity) should not exceed 160 mg %.

The Notification by the Director of Environmental Health Bureau of the Ministry of Health and Welfare describes heat treatment as means of decreasing the total pheophorbide amount and the existing pheophorbide amount. However, such heat treatment poses such a problem of quality control that the contained β-carotene is easily oxidized and therefore degraded, resulting in a decrease in β-carotene contained in dried powder product.

In particular, in culture facilities used outside for commercial mass-culturing of the algae belonging to the genus *Dunaliella*, the liquid temperature increases due to an elevation of temperature in summer, and therefore the total pheophorbide amount and the existing pheophorbide amount in summer tend to be higher than those in winter. Since more sufficient heat treatment is required in summer than in winter, there has been a serious problem in quality control that β-carotene contained in a dried powder product is decreased.

The above-mentioned Japanese Patent Laid-Open No. 1997-203 certainly refers to a dried powder product of the algae belonging to the genus *Dunaliella*, but it does not refer to the above-mentioned problem in quality control regarding pheophorbide.

Furthermore, Japanese Patent Laid-Open No. 2001-161348 specifically refers to a method for producing a dried powder product of the algae belonging to the genus *Chlorella*, but it does not refer to the above-mentioned problem in quality control regarding pheophorbide.

Therefore, the present invention has an object to provide a method for producing a dried *Dunaliella* powder product containing β-carotene at a high concentration by suppressing the degradation of β-carotene as an active ingredient while decreasing a pheophorbide amount to a predetermined value or less in a step for producing a dried powder product even if the total pheophorbide amount and the existing pheophorbide amount of the cultured algae belonging to the genus *Dunaliella* are higher in summer.

SUMMARY OF THE INVENTION

That is to say, the present invention relates to a method for producing *Dunaliella* powder, which includes a pH adjusting step in which an alga belonging to the genus *Dunaliella* is allowed to be in a basic state of pH 9.5 or higher in a step of producing a powder product of the alga belonging to the genus *Dunaliella*.

The alga belonging to the genus *Dunaliella* may be *Dunaliella bardawil*.

A *Dunaliella* powder product may be a product produced by the above-mentioned production method, wherein a total pheophorbide amount is 160 mg % or less, an existing pheophorbide amount is 100 mg % or less, and 3 to 20 g of β-carotene is contained in 100 g of the *Dunaliella* powder.

According to the method for producing *Dunaliella* powder of the present invention including a pH adjusting step in which an alga belonging to the genus *Dunaliella* is allowed to be in a basic state of pH 9.5 or higher in a step of producing a powder product of the alga belonging to the genus *Dunaliella*, it is possible to provide dried *Dunaliella* powder containing β-carotene at a high content by suppressing degradation of β-carotene as an active ingredient while decreasing each of the total pheophorbide amount and the existing pheophorbide amount to a predetermined value or less.

When the alga belonging to the genus *Dunaliella* is *Dunaliella bardawil*, it is possible to obtain a dried *Dunaliella* powder containing β-carotene at a higher content.

The *Dunaliella* powder product produced by the above-mentioned production method, which has a total pheophorbide amount of 160 mg % or less and an existing pheophorbide amount of 100 mg % or less, and contains 3 to 20 g of β-carotene in 100 g of the *Dunaliella* powder, can be used as health foods or health supplements, and raw materials for useful pharmaceutical preparations.

DETAILED DESCRIPTION OF THE PREFERRED EMBODIMENTS

A raw material to be used for carrying out a method for producing the present invention is microalgae, and preferably the algae belonging to the genus *Dunaliella* as one type of the green algae. The algae belonging to the genus *Dunaliella* are known to produce and store a large amount of β-carotene in the alga body. In particular, since *Dunaliella bardawil* and *Dunaliella salina* store a large amount of β-carotene in the alga bodies, they are further preferable to be used.

The algae belonging to the genus *Dunaliella* are cultured in a culture device such as a culture tank and a culture pool outside or inside for a predetermined time, and then pumped out from such a culture facility by using a pumping means such as a pump. The culture solution pumped out is filtered through a predetermined mesh net so as to remove foreign substances contaminated in the culture device.

The culture solution from which foreign substances are removed is dehydrated by a centrifuge so that the solid part in the culture solution is concentrated to a predetermined concentration. The concentration of the solid part in the culture solution after centrifugation is preferably 10 to 30% by weight from the viewpoint that the culture solution has fluidity although it is concentrated. Note here that the centrifuge is preferably an apparatus capable of carrying out centrifugation of the culture solution in a batch or continuous manner, and more preferably an apparatus capable of carrying out centrifugation continuously from the viewpoint of workability and productivity. Furthermore, as a centrifuge, generally available centrifuges are used, and the rotation rate of a rotor of the centrifuge is not particularly limited but it is set for each centrifuge used so as to have the above-mentioned concentration of the solid part of the culture solution.

In the present invention, a pH adjusting step is carried out in which a culture solution concentrated to a predetermined concentration is treated in a basic state. In the pH adjusting step, a basic compound, its aqueous solution or the like is added to the culture solution concentrated to a predetermined concentration, and the culture solution is preferably stirred and mixed with a stirring device such as a stirrer in a highly basic state in which the hydrogen ion exponent, i.e., pH is 9.5 or higher at a temperature of 25° C., more preferably stirred and mixed in a highly basic state in which pH is 10.0 or higher, and most preferably stirred and mixed in a highly basic state in which pH is 11.0 or higher. It is not preferable that pH is less than 9.5 because it is difficult to stably control *Dunaliella* powder so as to have a total pheophorbide amount of 160 mg % or less and an existing pheophorbide amount of 100 mg % or less throughout the year.

Note here that in general, in the production step of *Dunaliella* powder, various steps are usually carried out in neutral to weak basic states. If pH adjusting treatment is added as in the present invention, not only another step is added, but also a neutralization treatment step is carried out if necessary as mentioned below. For such reasons, productivity and the like may be affected. Therefore, conventionally, an idea of allowing a culture solution concentrated to a predetermined concentration to be in a strong basic has not been reached.

Preferable examples of basic compounds to be used in the pH adjusting step include lithium hydroxide, sodium hydroxide, potassium hydroxide, rubidium hydroxide, cesium hydroxide, tetramethylammonium hydroxide, calcium hydroxide, strontium hydroxide, barium hydroxide, thallium hydroxide, and guanidine. More preferable examples include widely used sodium hydroxide, potassium hydroxide, and calcium hydroxide. Furthermore, two or more thereof may be used together. In addition, an aqueous solution thereof having an arbitrary concentration can be used.

If necessary, after the pH adjusting treatment is carried out, a neutralization treatment step is carried out in order that the liquid property is made to be in a neutral range around pH 7 at a temperature of 25° C. This step will be necessary in the case where it is difficult to distribute *Dunaliella* powder at such a high pH when, for example, the obtained *Dunaliella* powder is sold as health foods or processed foods. Note here that if another neutralization treatment step is carried out when processed foods are produced using the *Dunaliella* powder, the neutralization treatment step is not necessarily carried out in the present invention.

As compounds to be used in the neutralization treatment step, an inorganic acid or an organic acid is used. Examples of the inorganic acid include hydrochloric acid, phosphoric acid, sulfuric acid, and nitric acid. Examples of the organic acid include formic acid, acetic acid, citric acid, and oxalic acid. Furthermore, two or more thereof may be used together. In addition, aqueous solutions thereof having an arbitrary concentration can be used.

Then, for removing dissolved salt or precipitated salt contained in the *Dunaliella* culture solution as well as salt generated in the neutralization treatment step, a desalting treatment step can be carried out. For the desalting treatment step, well-known methods can be used. For example, desalting treatment using a chitosan solution, which is described in Japanese Patent Laid-Open No. 1995-000147, can be used.

Then, in the present invention, for further decreasing pheophorbide harmful to a human body, which is contained in a culture solution subjected to desalting treatment and concentrated to a predetermined concentration, or for killing general bacteria, a heat treatment step may be carried out at a predetermined temperature for a predetermined time. By combining it with the above-mentioned pH adjusting treatment step, various pheophorbide amounts can be decreased more effectively. The heat treatment step is carried out preferably in a temperature range from 70° C. to 140° C., and more preferably in a temperature range from 80° C. to 130° C. It is not preferable that heat treatment temperature is carried out at a temperature of less than 70° C. because it takes a long time to decrease various pheophorbide amounts or carry out sterilization and the content of β-carotene in *Dunaliella* powder is lowered due to oxidative degradation. Furthermore, it is not preferable that heat treatment is carried out at a temperature of more than 140° C. because although it is possible to decrease various pheophorbide amounts or carry out sterilization in a very short time, the content of β-carotene in *Dunaliella* powder is also lowered due to oxidative degradation. Furthermore, time necessary for the heat treatment step is preferably in the range from 2 to 80 min, and more preferably in the range from 5 to 60 min. It is not preferable that heat treatment time is less than 2 min because various pheophorbide amounts cannot be decreased or sterilization sufficiently for selling as health foods and the like cannot be performed. It is not preferable that heat treatment time is longer than 80 min because β-carotene cannot be obtained at a high content due to oxidative degradation. Note here that the heat treatment step is not necessarily carried out after the desalting treatment step, but it may be carried out in arbitrary orders, for example, it is carried out before the pH adjusting treatment step.

Then, paste, which has been obtained after a neutralization treatment step or heat treatment step if necessary, is formed into a dried powder product by removing water from the paste by well-known methods such as spray drying, or lyophilization under decreased pressure.

The *Dunaliella* powder obtained in the above-mentioned series of methods has a total pheophorbide amount of 160 mg % or less and an existing pheophorbide amount of 100 mg % or less, and contains 3 to 20 g of β-carotene in 100 g of the *Dunaliella* powder. Furthermore, the amount of β-carotene contained in 100 g of the *Dunaliella* powder differs depending upon the algae belonging to the genus *Dunaliella* to be used as a raw material, but the amount is more preferably 5 to 15 g, and most preferably 6 to 10 g. It is not preferable that the amount of β-carotene contained in 100 g of the *Dunaliella* powder is less than 3 g because a commercial value thereof is lowered. Furthermore, in order to achieve a content of 20 g or higher, the algae belonging to the genus *Dunaliella* as the raw material is required to contain more β-carotene. However, such products are not known at the filing date of the application, and are not realistic and not preferable.

EXAMPLES

Next, Examples, Comparative Examples and Reference Example in accordance with the present invention will be described more specifically. Note here that the below-mentioned Examples are preferable specific examples for carrying out the present invention, and therefore various limits are made technically, but the present invention is not intended to be limited to these embodiments unless otherwise noted that the present invention is limited only to the Examples.

Example 1

*Dunaliella bardawil* cultured in a culture pool was pumped up by an electrically-driven pump, and allowed to filter through a stainless wire net having a sieve opening of 1 mm to remove foreign substances. Then, a culture solution containing *Dunaliella bardawil* from which foreign substances had been removed was separated continuously with a centrifuge having a rotor rotation speed of 4200 rpm, and the culture solution was concentrated into a paste state having a solid content of 15% by weight.

After that, 10% by weight of sodium hydroxide aqueous solution was added to the concentrated paste so that pH was 9.5 at 25° C. Then, the basic culture solution was subjected to pH adjusting treatment by stirring with a stirrer at 25° C. to 30° C. for one hour.

Then, 10% by weight of aqueous solution of hydrochloric acid was added to the culture solution that had been subjected to the pH adjusting treatment so that pH was 6.5 to 7.0 at 25° C. Then, the basic culture solution was subjected to neutralization treatment by stirring with a stirrer at 25° C. to 30° C. for 20 min.

Then, 0.5% by weight of aqueous solution of chitosan was gradually added to 100 parts by weight of the neutralized culture solution while the culture solution was stirred at 25° C. to 30° C. After addition, the stirring speed was decreased to about one-third, and then stirring was stopped. Then, after *Dunaliella* precipitated, an upper layer solution was removed and the precipitates were taken out, and thus desalting treatment was carried out.

Then, the paste-like precipitate containing water was formed into mist-like fine particles by a spray dryer method using a spray, and dried by heating in the conditions in which an inlet port temperature was 190° C. and an outlet port temperature was 90° C. to obtain dried powder.

Examples 2 to 4

Examples in Examples 2 to 4 were carried out in the same manner as in Example 1 except that pH in the pH adjusting treatment step was changed to the conditions described in Table 1 to obtain powder from the cultured *Dunaliella bardawil*.

Comparative Examples 1 to 6

Comparative Examples in Comparative Examples 1 to 6 were carried out in the same manner as in Example 1 except that pH in the pH adjusting treatment step was changed to the conditions described in Table 1 to obtain powder from the cultured *Dunaliella bardawil*.

Reference Example

In Reference Example, the cultured *Dunaliella bardawil* was not subjected to the pH adjusting treatment step and the neutralization treatment step but subjected to the above-mentioned desalting treatment step, and lyophilized without carrying out a heat treatment step to be made into powder. Powder obtained by this method is not necessarily preferable for selling as health foods and the like from the viewpoint of various pheophorbide amounts, but β-carotene in the cultured *Dunaliella bardawil* is hardly lost and is contained.

<Measurement of Total Pheophorbide Amount and Existing Pheophorbide Amount in *Dunaliella* Powder>

The total pheophorbide amount and the existing pheophorbide amount in *Dunaliella* powder were measured according to test methods described in the attached document of the Notification by the Director of Environmental Health Bureau of the Ministry of Health and Welfare mentioned above.

Specifically, the existing pheophorbide amount was analyzed by the following method. To 100 mg of the *Dunaliella* powder, 20 ml of 85% by volume of aqueous acetone was added, and the mixture was ground. After that, the supernatant was transferred to a centrifuge tube, and the same operation was carried out by adding 10 ml each of acetone to the residue. The respective supernatants were transferred to a centrifuge tube, and then the centrifugation was carried out, respectively. The supernatant was transferred to a separatory funnel containing 30 ml of ethyl ether. Then 50 ml of 5% sodium sulfate was added to the ether-acetone mixture solution, the solution was gently shaken to remove a sodium sulfate layer. Furthermore, the washing operation was repeated three times, sodium sulfate anhydrate was added thereto to carry out dehydration, and then, an ether layer was taken out, which was made to have a total amount 50 ml with ethyl ether to obtain a coloring agent stock solution. 20 ml of the coloring agent stock solution was taken, and then shaken and extracted with 20 ml and 10 ml each of 17% hydrochloric acid, respectively, and then a hydrochloric acid layer was transferred to a separatory funnel containing 150 ml of saturated sodium sulfate solution and 20 ml of ethyl ether. This was shaken and extracted, an ether layer was taken out separately, and ethyl ether was added thereto so that the total amount was 20 ml to obtain an extract of the degradation product. This extract of the degradation product was accurately diluted with ethyl ether to a necessary concentration, and then, the absorbance at 667 nm was measured with an ultraviolet-visible spectrophotometer. The amount of chlorophyll degradation product is calculated from the absorbance of pheophorbide a, the standard product, so as to obtain the existing pheophorbide amount (mg %).

The total pheophorbide amount was calculated as a sum of the existing pheophorbide amount and the chlorophyllase activity. The chlorophyllase activity was analyzed by the following method. 100 mg of the *Dunaliella* powder was precisely weighed, and a phosphate buffer solution of pH 8.0 and 10 ml of 70% by volume aqueous acetone were added thereto, the resultant mixture was incubated at 37° C. for three hours. After that, the solution was made to be weakly acidic with 10% by weight hydrochloric acid, and the amount of pheophorbide was measured according to the above-mentioned measurement method of the existing pheophorbide amount, and the increased amount was calculated by subtracting the existing pheophorbide amount from the measured value, and the increased amount was defined as a chlorophyllase activity (mg %).

<Measurement of β-carotene Content in *Dunaliella* Powder>

The contents of β-carotene in the *Dunaliella* powder obtained in Examples, Comparative Examples and Reference example were analyzed by high performance liquid chromatography (hereinafter, referred to as "HPLC") after general extract of the *Dunaliella* powder was carried out.

Specifically, the analysis was carried out by the following method. To 50 mg of the *Dunaliella* powder, 5 ml each of dichloromethane and acetone was added for extraction followed by centrifugation and the upper layer was removed. To the residue, 10 ml of hexane was added, and the mixture was shaken for extraction. The upper layer was mixed with the previously obtained upper layer. This operation was repeated until the color disappeared. Then, the solution was concentrated with an evaporator, and then hexane was added so that the total amount was 100 ml. This was subjected to quantification from the peak area ratio by HPLC based on a calibration curve that had previously been obtained from a β-carotene reagent. Then, the obtained amount of β-carotene was converted into a content amount per 100 g of *Dunaliella* powder. Note here that β-carotene of the present invention includes not only all-trans-β-carotene, that is, an isomer in which all the double bonds are trans-form, but also 9-cis-β-carotene, that is, an isomer in which only the 9th position is a cis-form.

The HPLC conditions were as follows.
Detector: Ultraviolet-Visible Spectrophotometer Detector (SPD-6AV, Shimadzu corp.)
Column: YMC-Pack AM-301 120A (4.6 mmi.d.kakeru 100 mm)
Mobile phase: hexane:benzene:methanol (15:25.5:59.5)
Flow rate: 1.0 ml/min
Wavelength: UV-453 nm The content of β-carotene in *Dunaliella* powder, the total pheophorbide amount and the existing pheophorbide amount are shown in Table 1 along with conditions for the pH adjusting treatment step of Examples, Comparative Examples and Reference Example. Note here that in Table 1, a production method with which the total pheophorbide amount was 160 mg % or less, the existing pheophorbide amount was 100 mg % or less, and the content of β-carotene in *Dunaliella* powder was 7% by weight or more was evaluated to be good.

TABLE 1

|  |  | EXAMPLES | | | | COMPARATIVE EXAMPLES | | | | | | REFERENCE EXAMPLE |
|---|---|---|---|---|---|---|---|---|---|---|---|---|
|  |  | 1 | 2 | 3 | 4 | 1 | 2 | 3 | 4 | 5 | 6 |  |
| pH ADJUSTING TREATMENT STEP | pH | 9.5 | 10.0 | 11.0 | 12.0 | 4.0 | 5.0 | 6.0 | 7.0 | 8.0 | 9.0 | — |
| TOTAL PHEOPHORBIDE | mg % | 118 | 111 | 102 | 103 | 193 | 156 | 167 | 155 | 130 | 124 | 173 |
| EXISTING PHEOPHORBIDE | mg % | 96 | 90 | 60 | 60 | 125 | 125 | 117 | 112 | 110 | 105 | 111 |
| CONTENT OF β-CAROTENE IN DUNALIELLA POWDER | g/100 g | 7.6 | 7.6 | 7.2 | 7.2 | 5.6 | 6.0 | 6.4 | 7.0 | 7.7 | 7.6 | 7.8 |

From these results, in order to produce β-carotene-rich powder products, which has a total pheophorbide amount of 160 mg % or less and an existing pheophorbide amount of 100 mg % or less and which is capable of being used as health foods or health supplement foods, or further raw materials of useful pharmaceutical preparations, from the culture algae belonging to the genus *Dunaliella*, it is found to be preferable that a pH adjusting treatment step is introduced and pH at 20° C. is 9.5 or higher.

Examples 5 to 8

In Examples in Examples 5 to 8, the pH adjusting treatment step was carried out in the conditions in which pH was adjusted as described in Table 2, the neutralization treatment and the desalting treatment were carried out, then heat treatment was carried out in an autoclave at 105° C. for 5 min, and then drying was carried out by spray drying to obtain powder.

For the obtained powder, the total pheophorbide, the existing pheophorbide, and the content of β-carotene in the *Dunaliella* powder were analyzed, and furthermore, the content of 9-cis-β-carotene in β-carotene was calculated from the analysis result of the above-mentioned liquid chromatography. The results thereof are shown in Table 2.

TABLE 2

|  |  | Examples | | | |
| --- | --- | --- | --- | --- | --- |
|  |  | 5 | 6 | 7 | 8 |
| pH ADJUSTING TREATMENT STEP | pH | 10.5 | 11.0 | 11.5 | 12.0 |
| HEAT TREATMENT STEP | temperature (° C.) | 105 | 105 | 105 | 105 |
|  | time (min) | 5 | 5 | 5 | 5 |
| TOTAL PHEOPHORBIDE | mg % | 116 | 107 | 105 | 105 |
| EXISTING PHEOPHORBIDE | mg % | 73 | 62 | 65 | 62 |
| CONTENT OF β-CAROTENE IN *DUNALIELLA* POWDER | g/100 g | 6.7 | 7.1 | 7.1 | 7.0 |
| CONTENT OF 9-CIS-β-CAROTENE IN β-CAROTENE | % by weight | 46 | 55 | 54 | 53 |

In general, naturally existing β-carotene mainly has a geometric structure of all-trans-β-carotene in which all the double bonds are trans-form. However, among them, 9-cis-β-carotene having a geometric structure in which the 9th position is a cis-form is a useful compound because a cis-form carbon-carbon double bond is oxidized more easily as compared with that in a trans-form double bond, and therefore the 9-cis-β-carotene is oxidized and degraded earlier than the all-trans-β-carotene, and vitamin A (retinol) can be obtained.

A method for producing a dried powder product of *Dunaliella* in which the content of 9-cis-β-carotene is improved has not been known, but from the results shown in Table 2, it is shown that it is possible to provide a dried powder product of *Dunaliella*, in which a total pheophorbide amount is 160 mg % or less, an existing pheophorbide amount is 100 mg % or less, and 9-cis-β-carotene is contained at such a high concentration of 40% by weight or more with respect to β-carotene by suppressing degradation of 9-cis-β-carotene.

The invention claimed is:

1. A method for producing *Dunaliella* powder, comprising:
    a pH adjusting step in which a culture solution *Dunaliella bardawil* is adjusted to be in a basic state of pH 9.5 or higher;
    a heat treatment step in which the culture solution is heated in a temperature range from 70° C. to 140° C. for from 2 to 80 minutes; and
    after the pH adjusting step, subjecting the culture solution to a desalting treatment step.

2. The method for producing *Dunaliella* powder according to claim 1, wherein the culture solution comprises 10 to 30% of solids by weight.

3. The method for producing *Dunaliella* powder according to claim 1, further comprising a neutralization treatment step to produce a neutral range around pH 7 at a temperature of 25° C.

4. The method for producing *Dunaliella* powder according to claim 1, further comprising a water removal step.

5. The method for producing *Dunaliella* powder according to claim 1, wherein the pH adjusting step comprises adding a basic compound or an aqueous solution of a basic compound to the culture solution and stirring at 25° C. to 30° C. for one hour.

* * * * *